(12) United States Patent
Cech et al.

(10) Patent No.: US 7,940,479 B2
(45) Date of Patent: May 10, 2011

(54) POSITIONERS AND MICROSCOPES INCORPORATING THE SAME

(75) Inventors: Steven D. Cech, Aurora, OH (US); Gerald Kotnik, Willoughby, OH (US)

(73) Assignee: Volk Optical, Inc., Mentor, OH (US)

( * ) Notice: Subject to any disclaimer, the term of this patent is extended or adjusted under 35 U.S.C. 154(b) by 455 days.

(21) Appl. No.: 11/970,850

(22) Filed: Jan. 8, 2008

(65) Prior Publication Data

US 2008/0239524 A1  Oct. 2, 2008

Related U.S. Application Data

(60) Provisional application No. 60/909,532, filed on Apr. 2, 2007.

(51) Int. Cl.
*G02B 7/02* (2006.01)
(52) U.S. Cl. .................. 359/822; 359/823
(58) Field of Classification Search .......... 359/368, 359/694, 811, 819, 822–824; 351/110, 159, 351/160 R
See application file for complete search history.

(56) References Cited

U.S. PATENT DOCUMENTS

| | | | |
|---|---|---|---|
| 3,200,304 A | 8/1965 | Atkins et al. | |
| 3,254,313 A | 5/1966 | Atkins et al. | |
| 3,715,540 A | 2/1973 | Larson | |
| 4,190,322 A | 2/1980 | Wortley | |
| 4,695,137 A | 9/1987 | Jorgens et al. | |
| 4,807,989 A | 2/1989 | Nagano et al. | |
| 4,885,667 A | 12/1989 | Selden | |
| 4,887,193 A | 12/1989 | Dieckmann | |
| 4,963,903 A | 10/1990 | Cane | |
| 5,150,771 A * | 9/1992 | Porter | 188/67 |
| 5,339,799 A | 8/1994 | Kami et al. | |
| 5,495,286 A | 2/1996 | Adair | |
| 5,526,074 A | 6/1996 | Volk | |
| 5,694,212 A | 12/1997 | Weissman | |

(Continued)

FOREIGN PATENT DOCUMENTS

WO   WO 91/15150   10/1991

OTHER PUBLICATIONS

Bal Seal Engineering "Bal-Springs for Holding, Latching, Locking, and Compressing Applications", Bal-Spring Catalog DM-9, 2003.

(Continued)

*Primary Examiner* — Ricky L Mack
*Assistant Examiner* — Mahidere S Sahle
(74) *Attorney, Agent, or Firm* — Dinsmore & Shohl LLP

(57) ABSTRACT

In accordance with one embodiment of the present invention, a positioning device comprises a microscope assembly and a lens positioning assembly. The lens positioning assembly comprises a lens support subassembly and a bi-directional positioning guide. The lens support subassembly comprises a translating rod, while the positioning guide comprises a coiled spring. The coiled spring is canted relative to a longitudinal axis of the rod. The inner periphery of the coiled spring engages in a spring loaded state an outer periphery of the rod such that the coiled spring provides a frictional force about the outer periphery of the rod. This frictional force provided by the coiled spring about the outer periphery of the rod is sufficient to hold the rod within the inner periphery, but permit infinitely variable bi-directional movement of the rod through the inner periphery under an applied force. Additional embodiments are disclosed and claimed.

17 Claims, 12 Drawing Sheets

U.S. PATENT DOCUMENTS

| | | |
|---|---|---|
| 5,793,469 A | 8/1998 | Feiertag et al. |
| 5,793,524 A | 8/1998 | Luloh |
| 5,810,306 A | 9/1998 | Hung et al. |
| 5,847,883 A | 12/1998 | Rispoli, Sr. |
| 6,439,721 B1 | 8/2002 | Reiner et al. |
| 6,733,128 B2 | 5/2004 | Kirchhuebel |
| 6,788,455 B2 | 9/2004 | Kirchhuebel et al. |
| 6,916,000 B2 | 7/2005 | Weiss |
| 6,967,774 B2 | 11/2005 | Kirchhuebel et al. |
| 7,002,737 B1 | 2/2006 | Akiyama et al. |
| 7,092,152 B2 | 8/2006 | Kirchhuebel |
| 2004/0218266 A1 | 11/2004 | Kirchhuebel et al. |
| 2008/0013188 A1 | 1/2008 | Cech |

OTHER PUBLICATIONS

International Search Report and Written Opinion dated Aug. 19, 2008 pertaining to International application No. PCT/US2008/057298.

* cited by examiner

FIG. 10
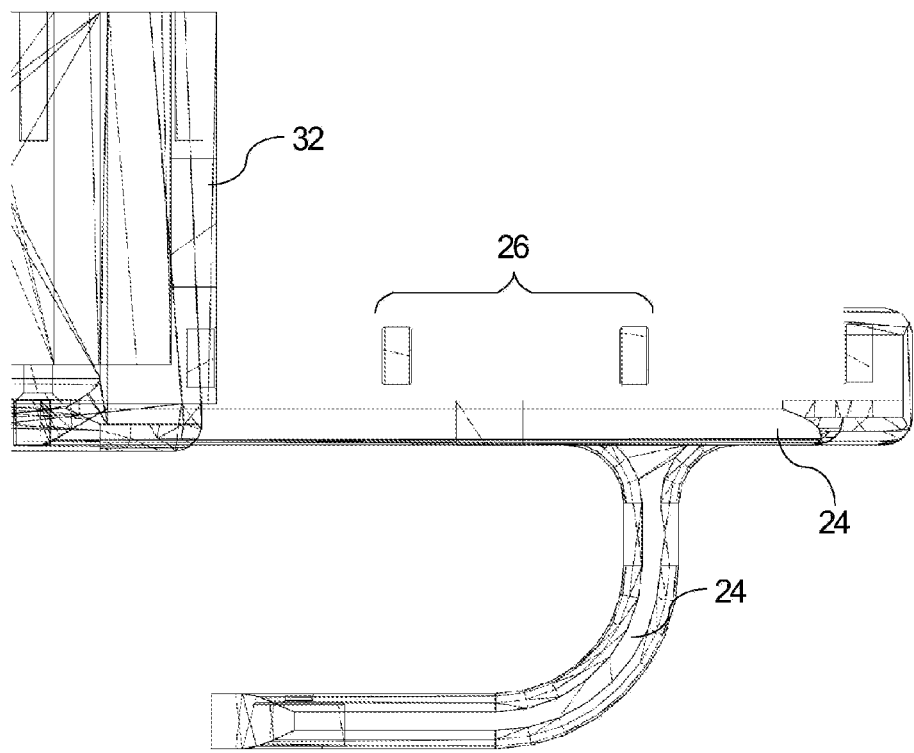
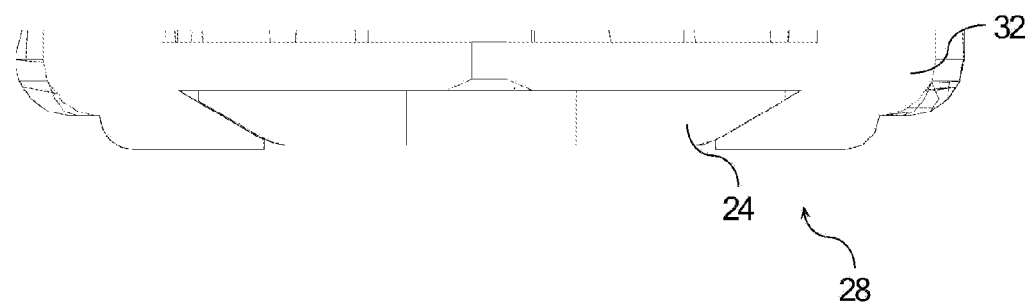
FIG. 11

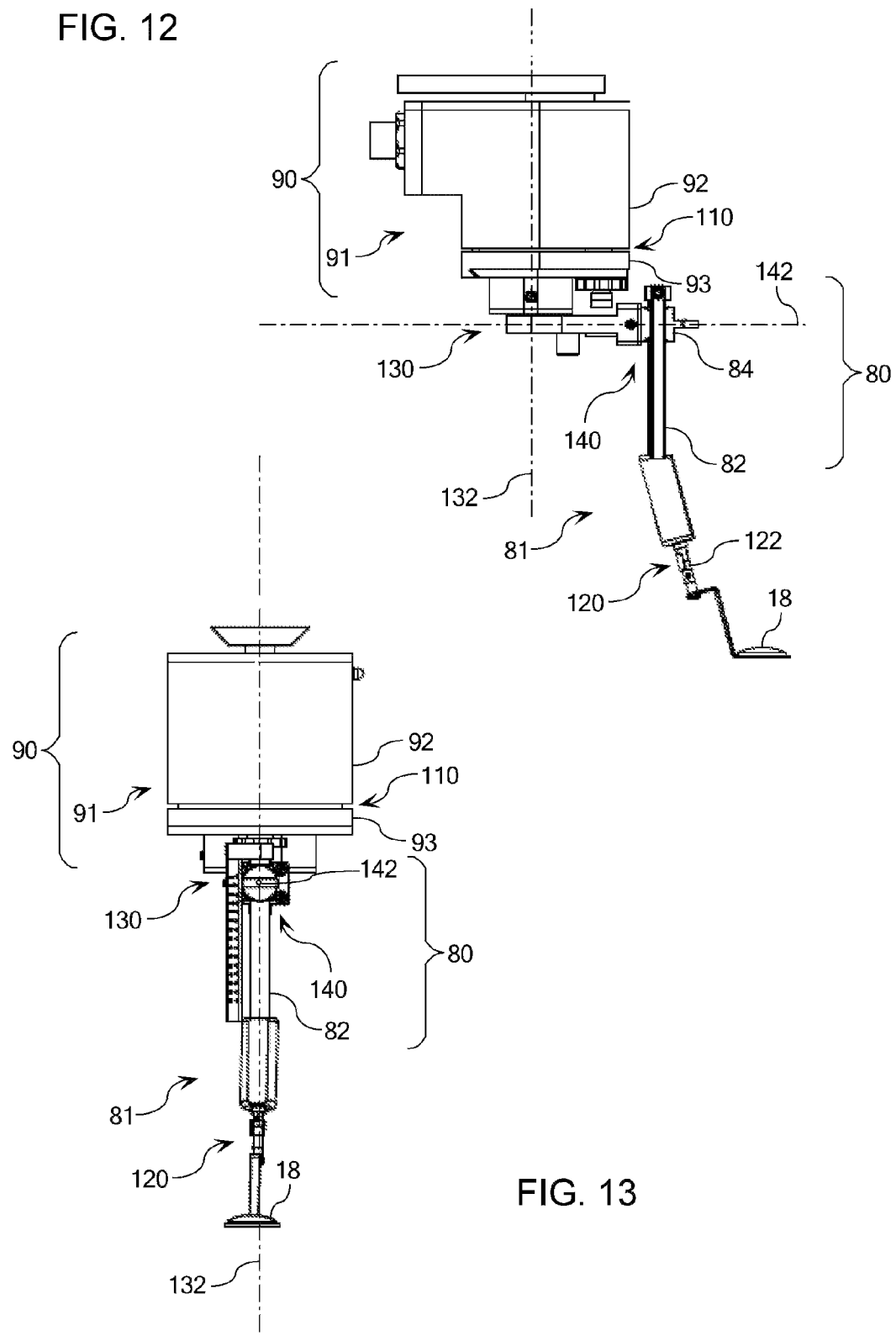

POSITIONERS AND MICROSCOPES INCORPORATING THE SAME

CROSS-REFERENCE TO RELATED APPLICATIONS

This application claims the benefit of U.S. Provisional Application Ser. No. 60/909,532 (VOL 0005 MA), filed Apr. 2, 2007.

BACKGROUND

Embodiments of the present invention relate to lens positioning in ophthalmic microscopy or other types of microscopy. The embodiments also relate more generally to controllable object positioning, without regard to whether the positioner or its individual components are used in microscopy.

BRIEF SUMMARY

In accordance with one embodiment of the present invention, a positioning device is provided comprising a first lens positioning assembly and a second lens positioning assembly. The first lens positioning assembly comprises a lens support subassembly and a bi-directional positioning guide. The lens support subassembly comprises a translating rod, while the positioning guide comprises a coiled spring. The coiled spring is canted relative to a longitudinal axis of the rod and the inner periphery of the coiled spring engages in a spring loaded state an outer periphery of the rod such that the coiled spring provides a frictional force about the outer periphery of the rod. The frictional force provided by the coiled spring about the outer periphery of the rod is sufficient to hold the rod within the inner periphery, but permit infinitely variable bi-directional movement of the rod through the inner periphery under an applied force. The second lens positioning assembly comprises an electromagnetic linear actuator configured to adjust bi-directionally a position of the lens support subassembly relative to a vertical position of the microscope.

In accordance with another embodiment of the present invention, a positioning device comprises a lens positioning assembly. The lens positioning assembly comprises a lens support subassembly and a bi-directional positioning guide. The lens support subassembly comprises a translating rod, while the positioning guide comprises a coiled spring defining an inner periphery. The inner periphery of the coiled spring engages in a spring loaded state an outer periphery of the rod such that the coiled spring provides a frictional force about the outer periphery of the rod. This frictional force provided by the coiled spring about the outer periphery of the rod is sufficient to hold the rod within the inner periphery, but permit infinitely variable bi-directional movement of the rod through the inner periphery under an applied force.

In accordance with yet another embodiment of the present invention, a positioning device comprising a lens positioner and a lens positioning assembly is provided. The lens positioner comprises a tension control assembly, an adjustable lens extension assembly, and a tensile cord. The tension control assembly is configured to control the degree of tension in the tensile cord. The adjustable lens extension assembly comprises a flexible linkage subassembly and a lens support subassembly. This flexible linkage subassembly comprises a proximal end and a distal end and is configured such that the distal end is movable relative to the proximal end through a plurality of degrees of freedom of movement. In addition, the flexible linkage subassembly is further configured such that the ease at which its distal end moves relative to its proximal end is a function of the degree of tension in the tensile cord. The lens positioning assembly comprises an electromagnetic linear actuator configured to adjust bi-directionally a position of the lens support subassembly relative to a vertical position of the microscope.

The present invention is not to be limited to the particular embodiments described herein. It is contemplated that additional embodiments are possible through modifications and variations to the embodiments described herein. Such modifications and variations are permissible without departing from the scope of the invention described in the specification and defined in the appended claims. For example, the scope of the present invention includes microscopes incorporating the various positioning devices described herein.

BRIEF DESCRIPTION OF THE DRAWINGS

The following detailed description of specific embodiments of the present invention can be best understood when read in conjunction with the following drawings, where like structure is indicated with like reference numerals and in which:

FIGS. 10 and 11, where FIG. 10 is an exploded view and FIG. 11 is taken in cross section, illustrate portions of a tension control assembly according one embodiment of to the present invention;

FIGS. 12 and 13 are illustrations of a lens positioning assembly according to another embodiment of the present invention.

Figure 1:
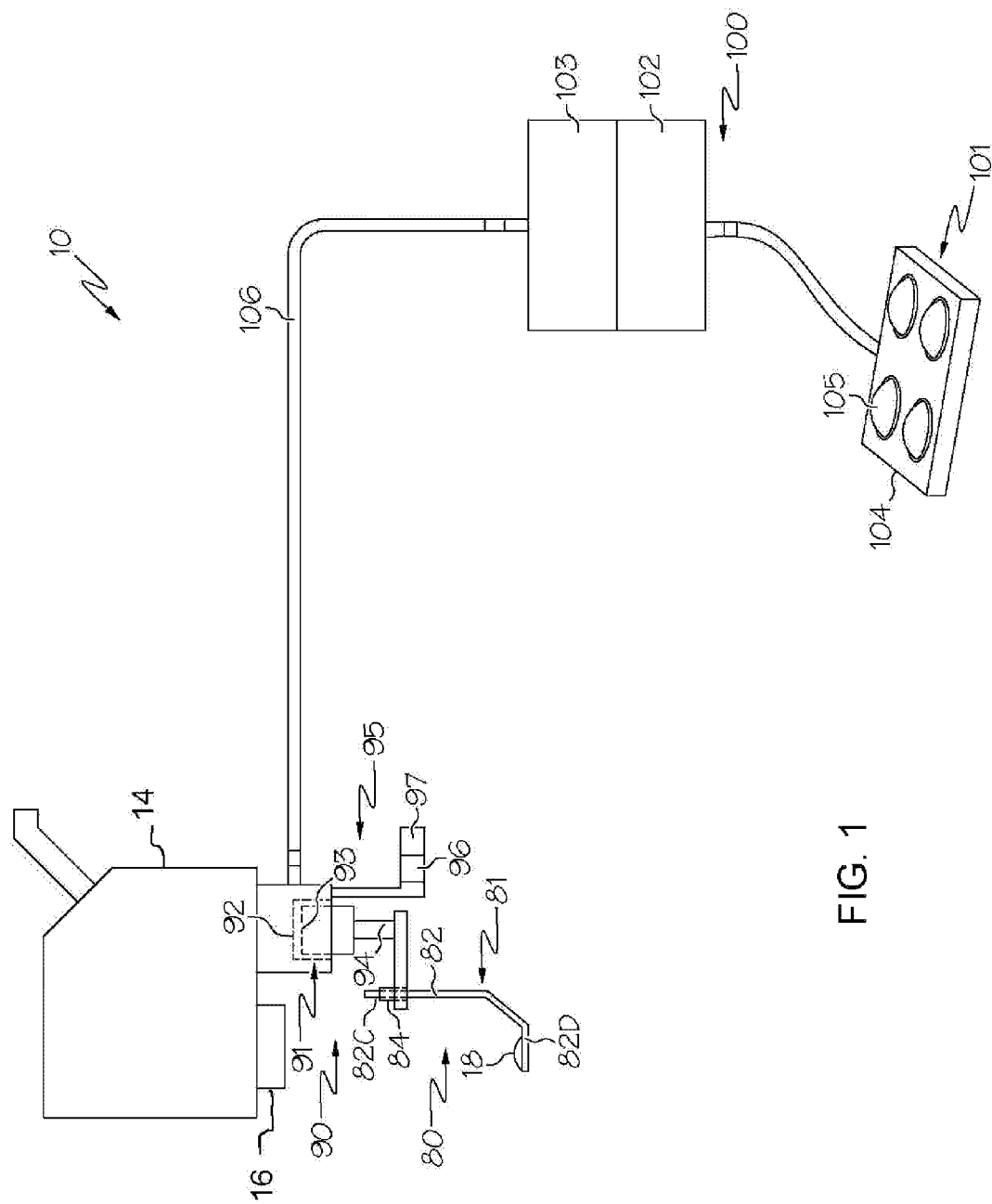
FIG. 1 is an illustration of an ophthalmic microscope in accordance with one embodiment of the present invention.

The embodiments set forth in the drawings are illustrative in nature and are not intended to be limiting of the invention defined by the claims. Moreover, individual aspects of the drawings and the invention will be more fully apparent and understood in view of the detailed description.

DETAILED DESCRIPTION

Figure 4:
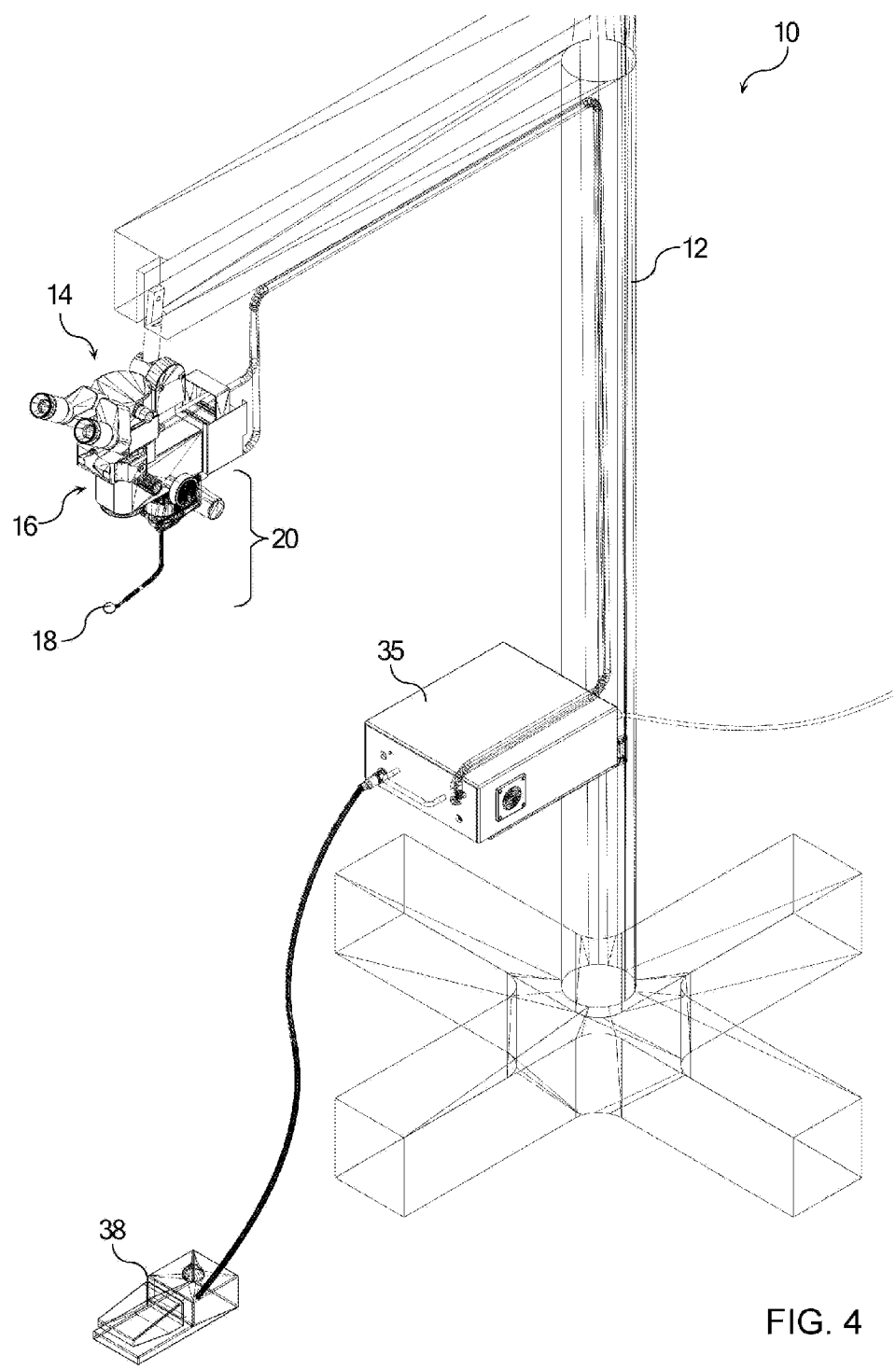
FIG. 4 is an illustration of an ophthalmic microscope incorporating a lens positioner according to one embodiment of the present invention.
Figure 5:
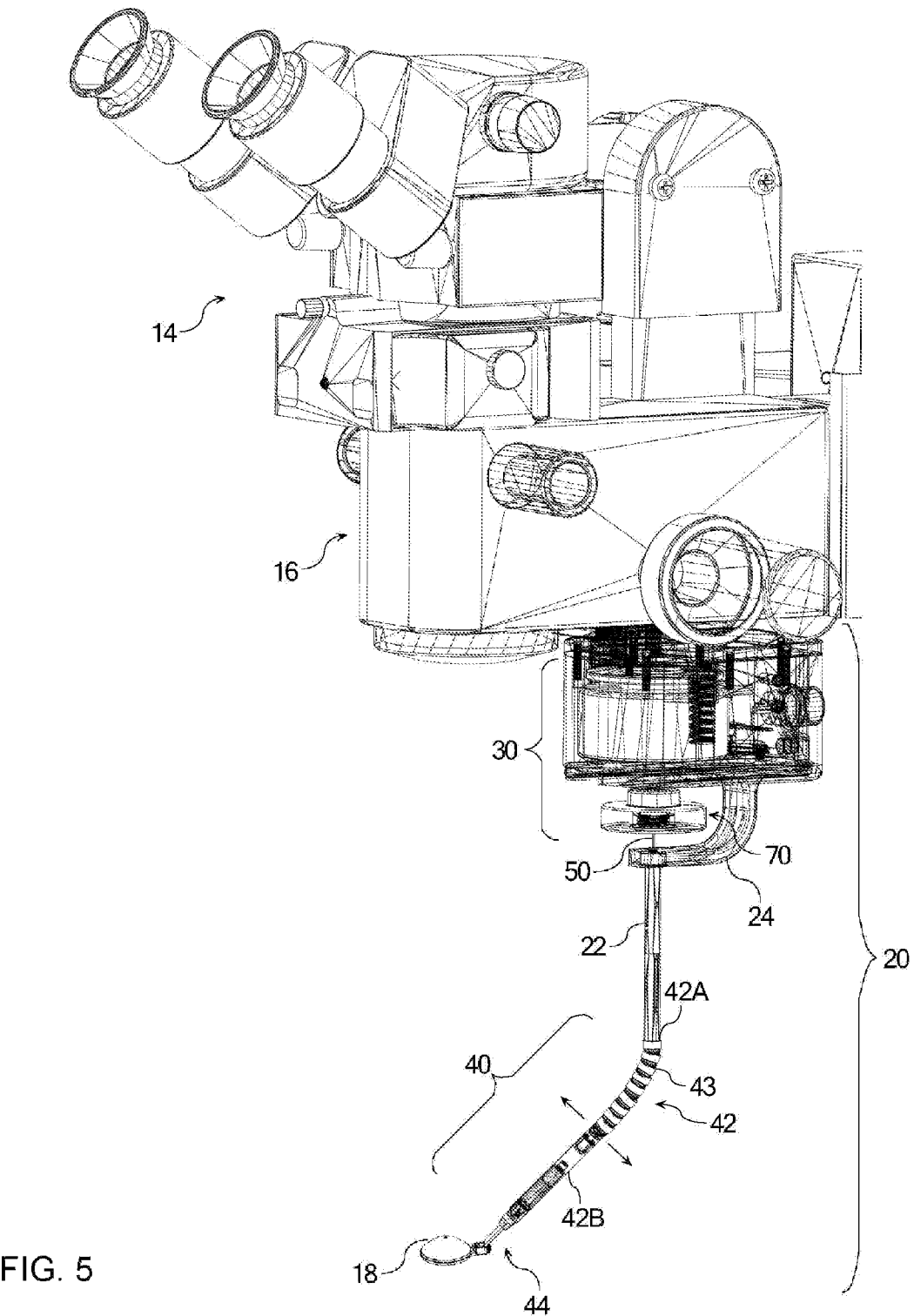
FIG. 5 is a magnified view of the microscope assembly and lens positioner illustrated in FIG. 4.

Referring initially to FIG. 1, the various concepts of particular embodiments of the present invention can be illustrated in the context of non-contact ophthalmic surgical microscope 10 comprising a microscope assembly 14, a first lens positioning assembly 80, and a second lens positioning assembly 90. More specifically, as will be appreciated by those familiar with the art of ophthalmic microscopy, ophthalmic microscopes, an example of which is illustrated in FIGS. 4 and 5, can be well configured for non-contact, high magnification, indirect imaging during vitreoretinal procedures. Generally, the ophthalmic microscope 10 includes a microscope assembly 14 and a wide angle lens 18. The microscope assembly and wide angle lens 18 cooperate to present the fundus image. In addition, this instrumentation enhances left/right eye image fusion, high efficiency light transmission, and optical transparency for improved views of the interior of the eye, although the concepts of the present invention are not limited to any particular microscope, viewing optics, or lens configuration.

Figure 2:
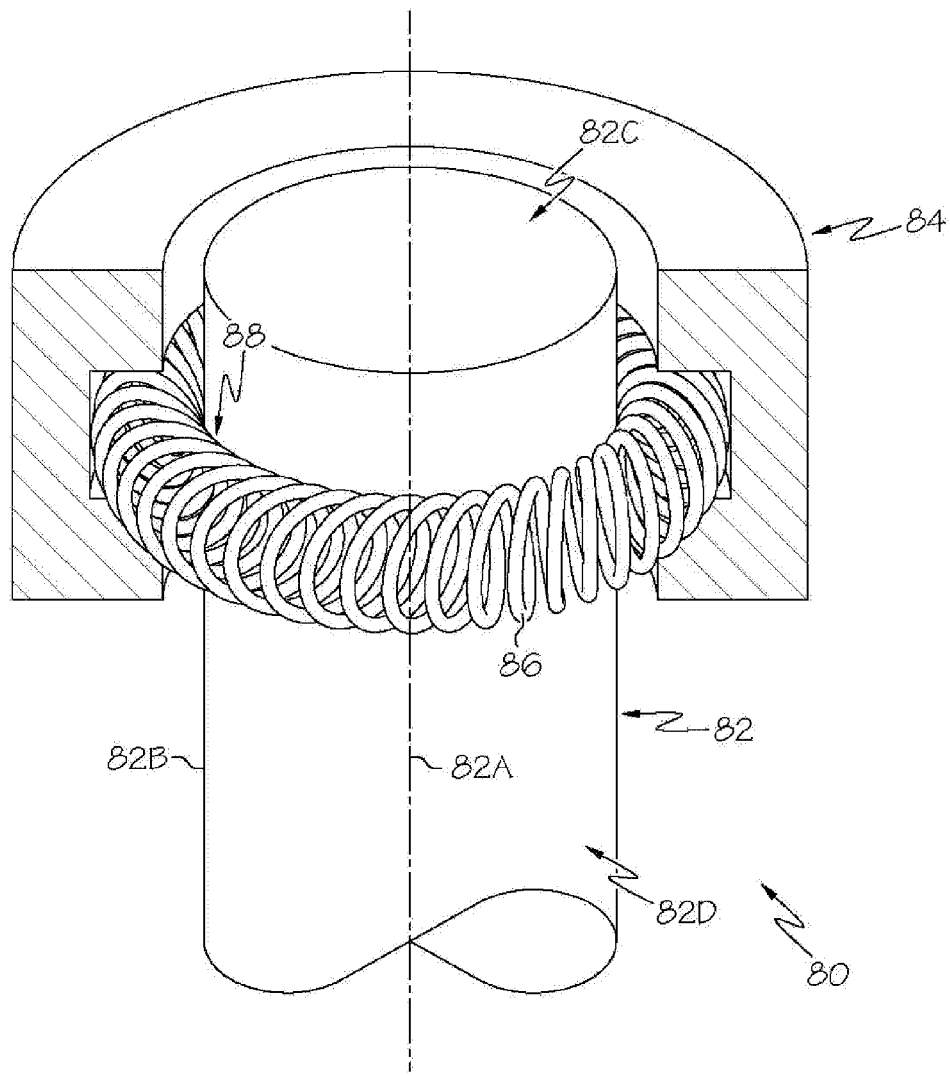
FIG. 2 is an illustration of a lens positioning assembly in accordance with one embodiment of the present invention.
Figure 14:
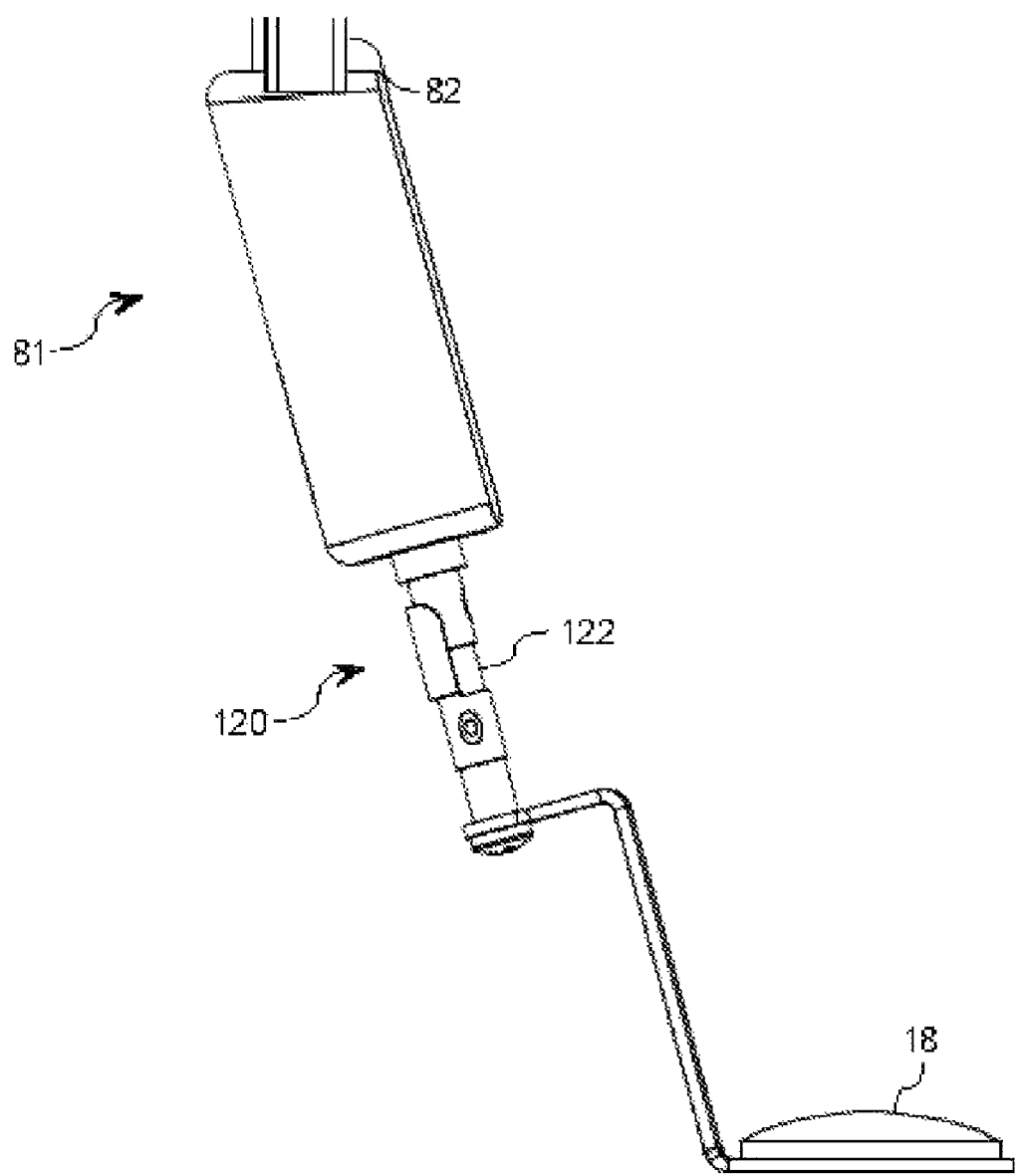
FIG. 14 is magnified view of a lens positioning hinge of an ophthalmic microscope according to one embodiment of the present invention.

As shown in FIGS. 1 and 2, the first lens positioning assembly 80 may comprise a lens support subassembly 81 and a bi-directional positioning guide 84. The lens support subassembly 81 comprises a translating rod 82. The lens support subassembly may also comprise a lens positioning hinge 120. As shown in FIGS. 12-14, this lens positioning hinge 120 may comprise an elastomeric cord 122 configured to permit movement of the lens 18 from a viewing position to a folded position away from the viewing position. The elastomeric cord 122 provides a degree of flexibility sufficient to permit movement of the lens 18 between the viewing position and the folded position.

As is clearly shown in FIG. 2, the positioning guide 84 comprises a coiled spring 86 wound about a circumscribed axis that extends around the translating rod 82 to define an inner periphery 88 of the coiled spring 86 and of the positioning guide 84. The circumscribed axis and the inner periphery 88 of the coiled spring 86 are concentric with one another. This coiled spring 86 may be canted relative to a longitudinal axis 82A of the rod 82. Generally, the inner periphery 88 of the coiled spring 86 engages in a spring loaded state an outer periphery 82B of the rod 82 such that the coiled spring 86 provides a frictional force about the outer periphery 82B of the rod 82. The translating rod 82, meanwhile, comprises a first end 82C configured to engage the inner periphery 88 of the coiled spring 86 of the positioning guide 84 and a second end 82D configured to support a lens, such as, but not limited to the wide angle lens 18. The frictional force provided by the coiled spring 86 about the outer periphery 82B of the rod 82 is sufficient to hold the rod 82 within the inner periphery 88 of the positioning guide 84, but permit infinitely variable bi-directional movement of the rod 82 through the inner periphery 88 under an applied force. This applied force can be that which would be exerted under manual adjustment of the rod 82 by an operator of the microscope 10.

The second lens positioning assembly 90 comprises an electromagnetic linear actuator 91 and does not generally include a motor, a lead screw, or other geared mechanism. As such, the electromagnetic linear actuator 91 is not susceptible to screw-backlash. According to one embodiment, the electromagnetic linear actuator comprises a voice coil actuator. Alternatively, the electromagnetic linear actuator may comprise a piezo-electric actuator.

The electromagnetic linear actuator 91 is configured to adjust bi-directionally a position of the lens support subassembly 81 relative to a vertical position of the microscope 10. Generally, the bi-directional movement of the translating rod 82 through the inner periphery 88 of the positioning guide 84 of the first lens positioning assembly 80 and the bi-directional adjustment of the first lens positioning assembly 80 by the electromagnetic linear actuator 91 are along parallel axes. More particularly, the electromagnetic linear actuator 91, shown in FIGS. 1 and 3, comprises a stationary component 92 and a bi-directionally moveable component 93 electromagnetically coupled to each other. According to one embodiment, the second lens positioning assembly functions as a fine adjustment assembly 95 configured to control the bi-directional movement of the moveable component. This fine adjustment assembly 95 may comprise a fine adjustment up switch 96 and a fine adjustment down switch 97, both electrically coupled to the electromagnetic linear actuator 91. More particularly, each switch 96, 97 can be coupled to any suitable control circuitry for operating the electromagnetic linear actuator 91. The moveable component 93 may be mechanically coupled to the positioning guide 84 of the first lens positioning assembly 80 such that bi-directional movement of the moveable component 93 correspondingly adjusts the position of the lens support subassembly 81 engaged to the positioning guide 84. According to one embodiment, the mechanical coupling may be provided where the second lens positioning assembly 90 comprises an extension subassembly 94 coupled to the bi-directional positioning guide 84 of the first lens positioning assembly 80, as is illustrated in FIG. 1.

As shown in FIG. 1, the microscope assembly 14 may comprise a power and control assembly 100. This power and control assembly 100 may be configured to control an operation of the electromagnetic linear actuator 91, as described above. More particularly, the power and control assembly 100 generally comprises an input device 101, a processor 102, and a power generator 103. The input device 101 may be configured to transmit commands inputted by an operator of the microscope 10. According to one embodiment, shown in FIG. 1, the input device 101 comprises a foot switch 104 comprising one or more pedals 105. These pedals 105 may permit an operator of the microscope assembly 14 to control remotely the bi-directional movement of the moveable component 93 of the electromagnetic linear actuator 91 and, thus, control the fine focus of the microscope. For example, one pedal 105 may be configured as a fine adjustment up switch, while another pedal 105 may be configured as a fine adjustment down switch.

The processor 102 may be configured to process the commands received from the input device 101 into instructions for the operation of the electromagnetic linear actuator 91. The power generator 103, meanwhile, may be configured to generate power sufficient to operate the electromagnetic linear actuator 91 according to the instructions of the processor 102. Cables 106 may be used to electrically couple the input device 101, the processor 102, the power generator 103, and the electromagnetic linear actuator 91. In addition, the microscope assembly 14 may further comprise a microscope stand 12, as shown in FIG. 4. The microscope stand 12 may be configured to support a microscope 10 in a position generally appropriate for conducting ophthalmic surgery.

According to another embodiment of the present invention, it is contemplated that the microscope need not necessarily comprise what is described above as the second lens positioning assembly comprising an electromagnetic linear actuator. Rather, the microscope 10 may merely comprise a microscope assembly 14 and the lens positioning assembly 80 described above with reference to FIG. 1.

Figure 3:
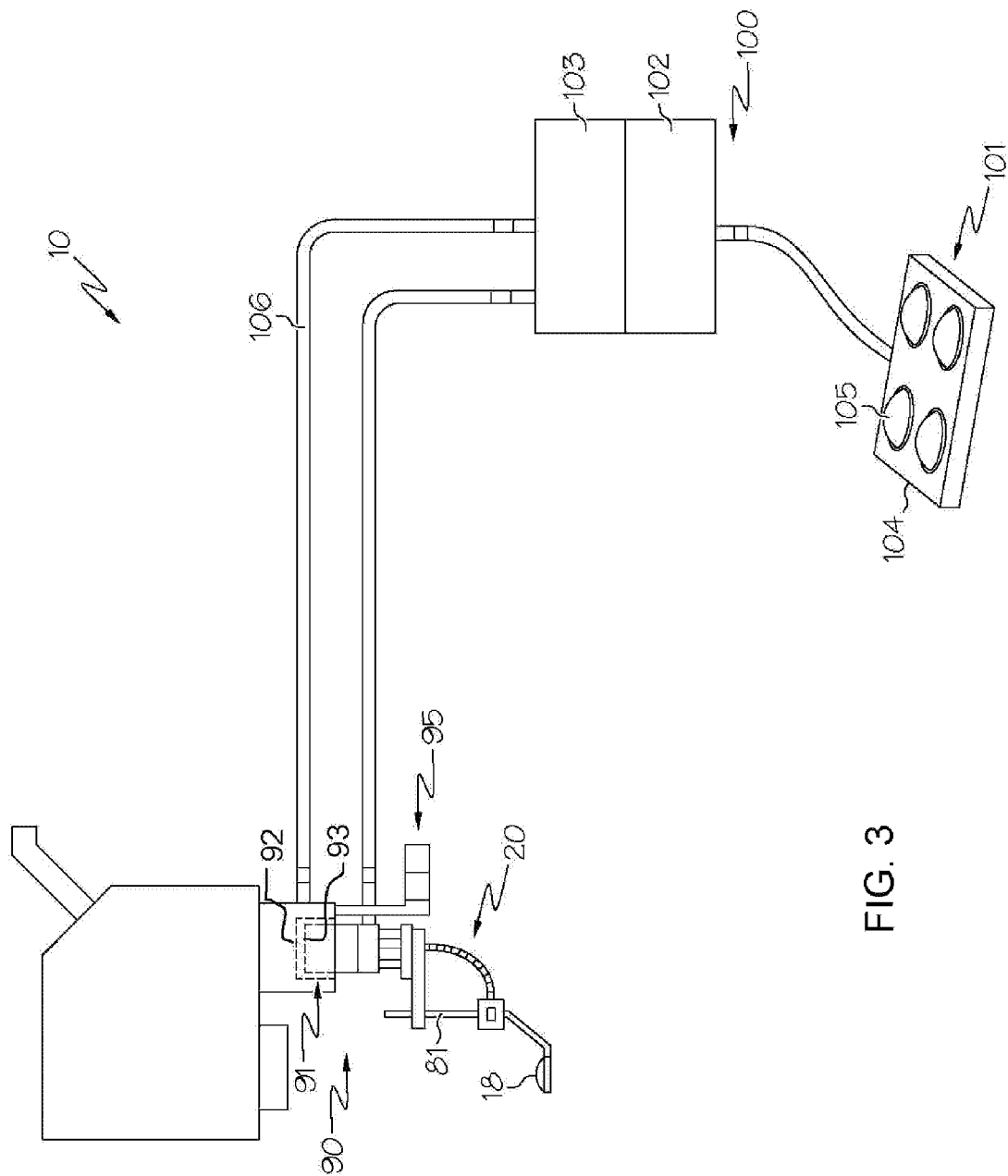
FIG. 3 is an illustration of an ophthalmic microscope according to another embodiment of the present invention.

According to yet another embodiment of the present invention, shown in FIG. 3, a microscope 10 may comprise a microscope assembly 14, a lens positioner 20, described in detail herein with reference to FIGS. 4-11, and a lens positioning assembly 90, described above with reference to FIG. 1.

In one embodiment of the present invention shown in FIGS. 12 and 13, a lens positioning assembly comprises an electromagnetic linear actuator 91 that is configured to define a gap 110 between the stationary component 92 and the bi-directionally moveable component 93 of the actuator 91. Further, the actuator 91, which may, for example, be configured as a voice coil actuator or another similar spring-loaded electromagnetic actuator, provides a spring-loaded cushion that permits movement of the stationary component 92 and the bi-directionally moveable component 93 toward each other across the gap 110. In this manner, any inadvertent collisions between the lens 18 or lens support subassembly 81 and an eye or other object under examination will be indirectly cushioned by the gap and the spring-loaded nature of the actuator 91, limiting damage to the object and a microscope 10.

According to yet another embodiment, also shown in FIGS. 12 and 13, the lens positioning assembly 80 comprises a lens support subassembly 81, a bi-directional positioning guide 84, a swivel assembly 130, and a pivot assembly 140. In this embodiment, the bi-directional positioning guide 84 engages a translating rod 82 of the lens support subassembly 81 to permit bi-directional movement of the translating rod 82. In addition, the swivel assembly 130 permits a swiveling of the lens support subassembly 81 about a swiveling axis 132. Also, the pivot assembly 140 permits a pivoting of the lens support subassembly 81 about a pivoting axis 142. The translating rod 82 and the swiveling and pivoting axes 132, 142 are oriented such that a lens 18 supported by the lens support subassembly 81 is permitted to move through a first degree of freedom of movement defined by the translating rod 82, a second degree of freedom of movement defined by the swiveling axis 132, and a third degree of freedom of movement defined by the pivoting axis 142. Further, the lens positioning assembly 81 is configured to permit simultaneous movement of a supported lens 18 through these first, second, and third degrees of freedom of movement.

It is contemplated that the bi-directional positioning guide 84 described herein may comprise one of a variety of different embodiments, all of which are configured to engage the translating rod 82 to permit bi-directional movement of the translating rod 82. For example, one embodiment of the bi-directional guide 84 may comprise the coil spring 86 described herein, while another embodiment of the bi-directional guide 84 may not comprise the coiled spring 86. It is also contemplated that an electromagnetic linear actuator 91 need not necessarily be used in conjunction with the embodiment comprising the swivel and pivot assemblies 130, 140. Rather, the actuator 91 and the swivel and pivot assemblies 130, 140 are illustrated together in FIGS. 12-14 merely for convenience purposes.

Referring to FIGS. 4 and 5, the lens positioner 20 comprises a tension control assembly 30, an adjustable lens extension assembly 40, and a tensile cord 50 coupling the tension control assembly 30 to the adjustable lens extension assembly 40, which comprises a flexible linkage subassembly 42 and a lens support subassembly 44. The flexible linkage subassembly 42 comprises a proximal end 42A and a distal end 42B and is configured such that the distal end 42B, i.e., the end to which the lens support subassembly 44 is secured, is movable relative to the proximal end 42A through a plurality of degrees of freedom of movement. This movement is partially illustrated by the directional arrows in FIG. 5.

The flexible linkage subassembly 42 is further configured such that the ease at which its distal end 42B moves relative to its proximal end 42A is a function of the degree of tension in the tensile cord 50. This degree of tension can be controlled on a selective basis by the tension control assembly 30. Accordingly, in operation, the tension control assembly 30 controls the degree of tension in the tensile cord 50 to permit or inhibit movement of the distal end 42B of the flexible linkage subassembly 42 relative to the proximal end 42A of the flexible linkage subassembly 42 on a selective basis, permitting adjustment and readjustment of the position of the wide angle lens 18 through multiple degrees of freedom.

Figure 6:
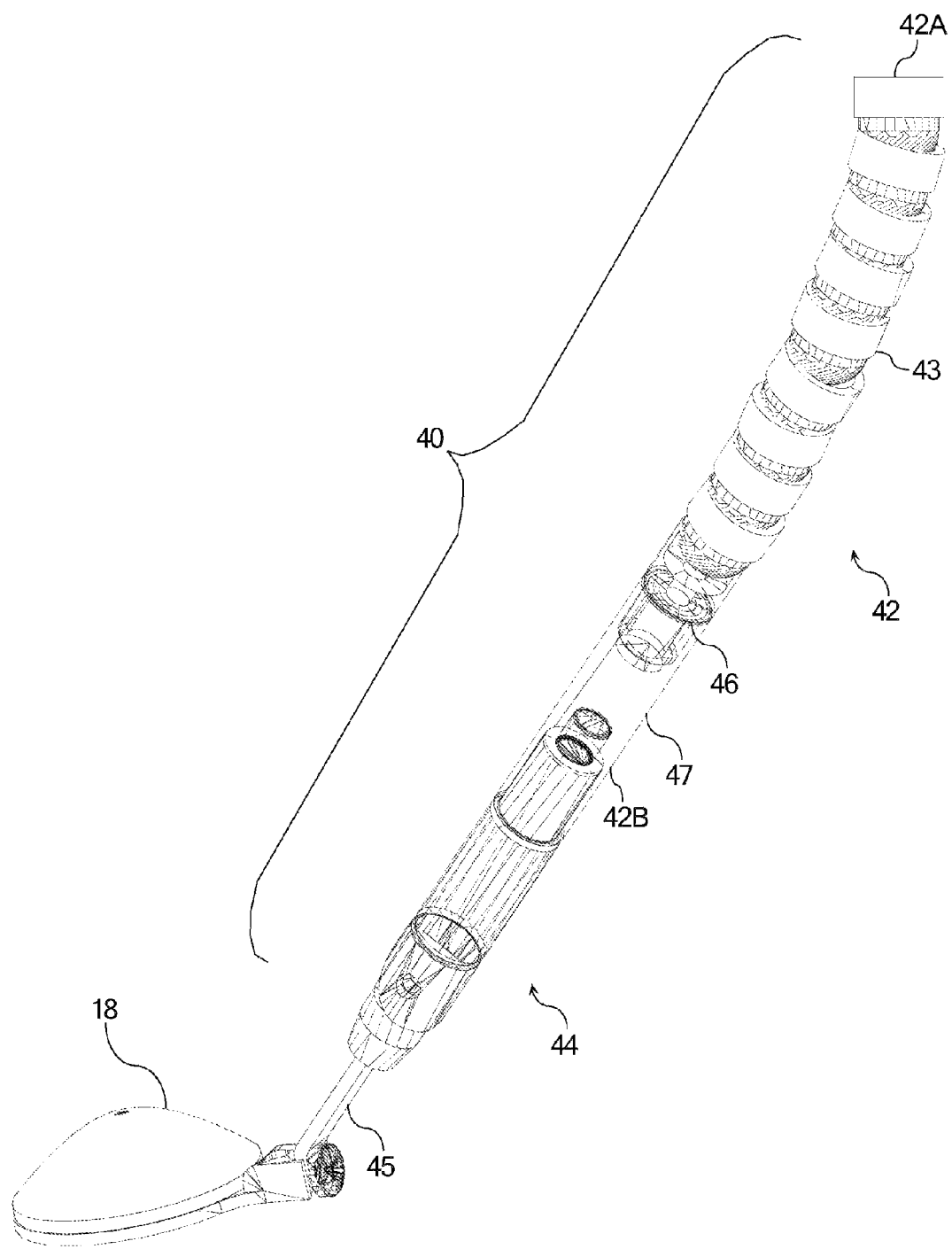
FIG. 6 is an illustration of an adjustable lens extension assembly in accordance with one embodiment of the present invention.
Figure 7:
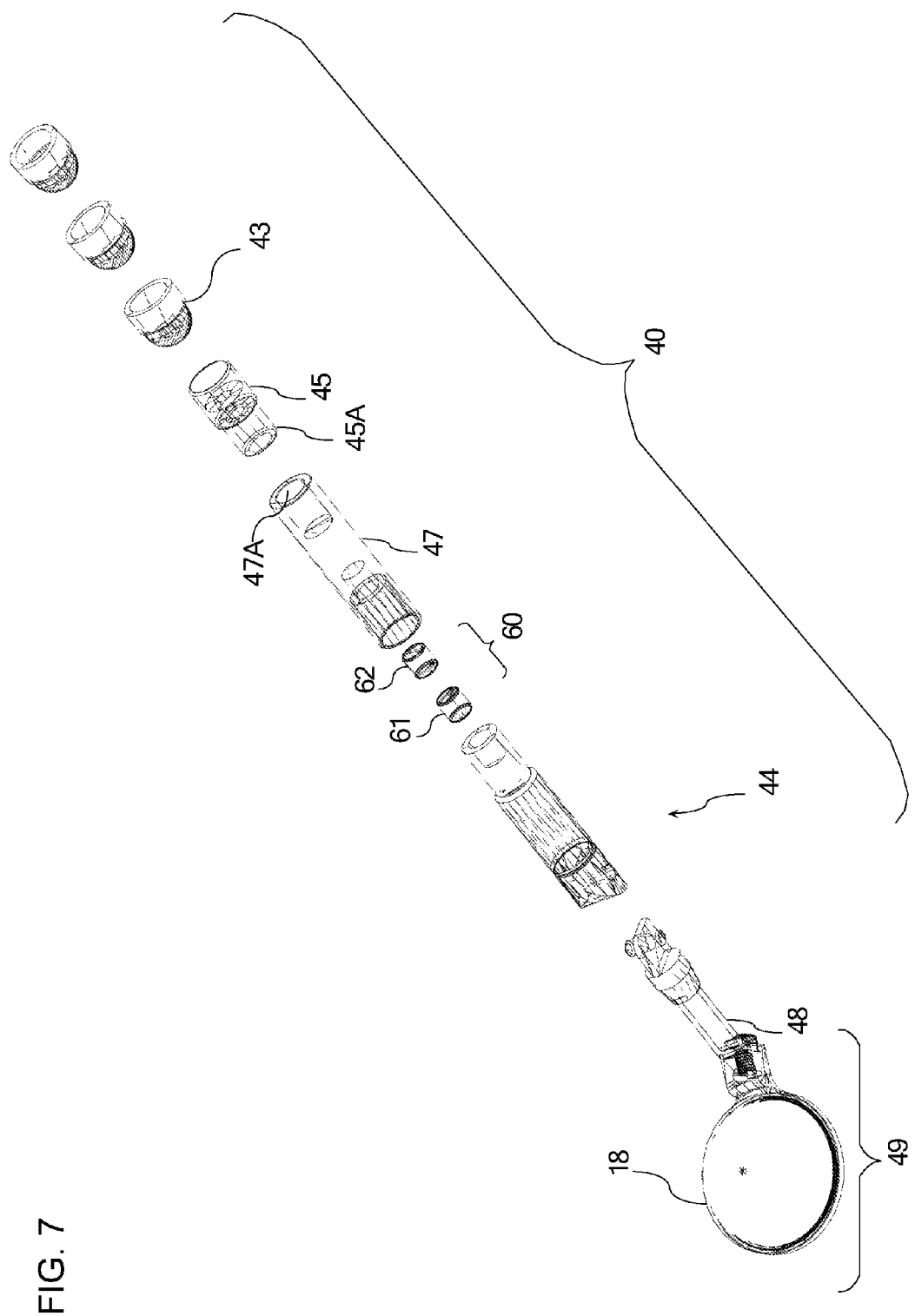
FIG. 7 is an exploded illustration of the adjustable lens extension assembly of FIG. 6.

A more detailed illustration of an adjustable lens extension assembly 40 according to one embodiment of the present invention is presented in FIGS. 6 and 7. As is noted above, the adjustable lens extension assembly 40 comprises the flexible linkage subassembly 42 and the lens support subassembly 44. The flexible linkage subassembly comprises a plurality of ball-and-socket type links 43, each comprising a central bore sufficient to accommodate passage of the tensile cord therethrough. Collectively, this series of ball-and-socket links exhibit a mechanical preference for immobility as the degree of tension in the tensile cord increases. Stated differently, when the tensile cord 50 is in a relatively relaxed but not unduly loose state, the distal end 42B of the flexible linkage subassembly 42 can be easily adjusted relative to the proximal end 42A of the flexible linkage subassembly 42. In contrast, when the tensile cord 50 is in a relatively taut state, it becomes more difficult to adjust the position of the distal end 42B of the flexible linkage subassembly 42. Typically, the degree of tension in the relatively taut state will be sufficient to lock the distal end 42 in a set position under normal microscope operating conditions. If readjustment is needed, the degree of tension in the tensile cord 50 can be relaxed to permit convenient movement of the distal end 42. For example, and not by way of limitation, it is contemplated that it will typically be sufficient to apply a load of up to about 100 lbs, or higher, to the tensile cord 50 to lock the position of the distal end 42 of the flexible linkage subassembly 40. In the relatively relaxed state, the load on the tensile cord 50 may drop as low as 5 lbs, or lower.

The lens positioner 20 may further comprise a coupling linkage 22 that can be used to indirectly couple the adjustable lens extension assembly 40 to a mechanical stop 24 provided by the tension control assembly 30. Referring to FIGS. 10 and 11, it is noted that the mechanical stop 24 can be secured to the remainder of the tension control assembly 30 via a magnetic coupling in the form of a pair of magnets 26, each of which can be secured within respective recesses formed in mating components of the tension control assembly 30, as is illustrated in detail in FIG. 10. The degree of securement attributable to the magnetic coupling is such that the mechanical stop 24 may be manually disengaged from the remainder of the tension control assembly 30 to facilitate maintenance, cleaning, or sterilization. As is illustrated in FIG. 11, the engagement of the mechanical stop to the remainder of the tension control assembly 30 can be enhanced by providing a sliding dovetail engagement, illustrated generally at 28. Of course, it is contemplated that any of a variety of conventional or yet to be developed hardware for releasably securing the mechanical stop 24 to the remainder of the tension control assembly 30 would fall within the scope of the present invention.

Referring further to FIGS. 6 and 7, it is noted that the flexible linkage subassembly 42 comprises a cord accommodating passage that extends from the proximal end 42A of the flexible linkage subassembly 40 to the distal end 42B of the flexible linkage subassembly 42. Further, the flexible linkage subassembly 42 comprises a cord anchor 46 at its distal end 42B, which anchor 46 is used to secure one end of the tensile cord 50. For the purposes of describing and defining the present invention, it is noted that the term "cord" is intended to refer broadly to any longitudinally extending tensile member, e.g., cable, wire, strand, linkage assembly, etc.

For the purposes of describing and defining the present invention, it is noted that a variety of structures may be employed in constructing the flexible linkage subassembly 42 including, but not limited to, the ball-and-socket type links described above or any other types of links or hardware that can be used to create a flexible extension that can be "locked" or "unlocked" in response to variations in tension applied to a tensile cord. For example, it is contemplated that any the flexible linkage subassembly incorporating friction-based locking hardware would fall within the scope of the present invention.

Referring further to FIG. 7, the flexible linkage subassembly 42 may comprise an adjustment arm 45 configured to permit selective adjustment of the tension in the tensile cord by reducing or extending the length of the flexible linkage subassembly 42. More specifically, in the illustrated embodiment, the adjustment arm 45 comprises an external threaded surface 45A that engages a complementary threaded bore 47A in sleeve 47. Accordingly, the degree of tension in the tensile cord 50 can be adjusted via the threaded engagement by rotating the adjustment arm 45 to alter the length of the flexible linkage subassembly 42, with longer lengths associated with increased tension and shorter lengths associated with less tension. The aforementioned selective adjustment of tension in the tensile cord will typically be employed to ensure sufficient degrees of tension in the taut and relaxed tensile states of the tensile cord 50, permitting the tension control assembly 30 and flexible linkage subassembly 42 to operate properly. The thrust bearing subassembly 70, described in detail below with reference to FIG. 9 may alternatively be employed to provide this type of adjustment.

FIGS. 6 and 7 also illustrate the lens support subassembly 44 in detail. In the illustrated embodiment, the lens support subassembly 44 is secured to the distal end 42B of the flexible linkage subassembly 42 via a magnetic coupling 60 comprising first and second magnets 61, 62, which are mounted within respective recesses formed in the distal end 42B of the flexible linkage subassembly 42 and a corresponding end of the lens support subassembly 44. Preferably, the degree of securement attributable to the magnetic coupling is such that the lens support subassembly 44 can be manually removed from the flexible linkage subassembly 42 to facilitate maintenance, cleaning, or sterilization, or to allow for convenient interchange of different lens support subassemblies 44 with the flexible linkage subassembly 42. Of course, it is contemplated that any of a variety of conventional or yet to be developed hardware for releasably securing the lens support subassembly 44 to the distal end 42B of the flexible linkage subassembly 42 would fall within the scope of the present invention.

The lens support subassembly 44 further comprises a hinged lens arm 48 and the adjustable lens extension assembly 40 further comprises a lens housing subassembly 49 secured to the lens support subassembly 44 via the hinged lens arm 48. The hinged lens arm provides a further point of control in adjusting the position of the wide angle lens 18.

Figure 8:
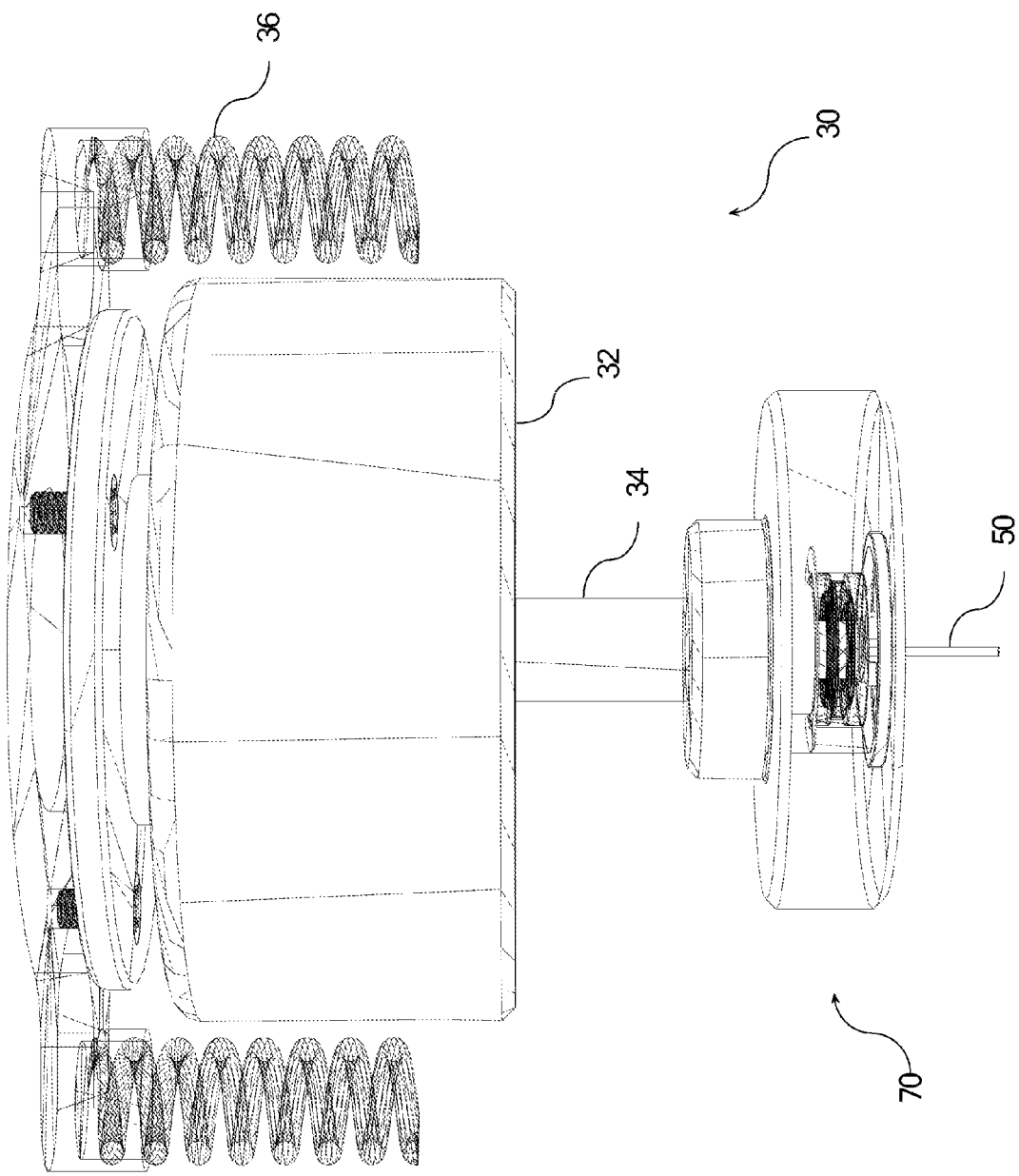
FIG. 8 is a perspective view of particular components of a tension control assembly according to one embodiment of the present invention.

Referring to FIG. 8, the tension control assembly 30 may comprise a solenoid actuated tension control mechanism 32 coupled to the tensile cord 50 via a thrust bearing subassembly 70 that is secured to opposing ends of the tensile cord 50 and a solenoid plunger 34 of the tension control assembly 30. The solenoid actuated tension control mechanism 32 places the tensile cord 50 in a relatively taut state when its solenoid is deactivated and in a relatively relaxed state when its solenoid is activated. Further, the tension control assembly 30 comprises a spring-loaded tension control mechanism (see springs 36) that places the tensile cord 50 in a relatively taut state when the tension control assembly is at rest. Although FIG. 8 specifically illustrates a solenoid actuated control mechanism 32, it is contemplated that a variety of other types of actuation mechanisms may be employed in the tension control assembly 30 of the present invention. For example, and not by way of limitation, it is contemplated that motor driven actuators, e.g., screw-based linear actuators, and solid state actuators, e.g., piezoelectric or magnetorestrictive actuators, may be employed without departing from the scope of the present invention.

Returning to FIG. 4, the tension control assembly 30 further comprises a controller 35 and a foot-activated switch 38 coupled to the controller 35. The controller 35, which includes a suitable power supply, and the foot-activated switch 38 cooperate to control actuation of the solenoid actuated tension control mechanism 32. Alternatively, the tension control assembly 30 may comprise touch-sensitive switching circuitry coupled to the controller 35 to enable selective actuation of the solenoid actuated tension control mechanism 32. Generally, the touch-sensitive switching circuitry and the controller 35 can be configured to provide an electrical switching response to human contact with selected portions of the flexible linkage subassembly 42, the lens support subassembly 44, the lens housing subassembly 49, or combinations thereof.

More specifically, the touch-sensitive switching circuitry comprises one or more electrical conductors that are conductively coupled to one or more electrically conductive touch sensitive areas of the adjustable lens extension assembly 40. In this manner, touch activation of the tension control assembly 30 will allow a user to adjust the position of the wide angle lens 18 without having to operate a foot pedal or any other peripheral switching device. Typically, when the touch sensitive control area is untouched, the positioner tension control assembly will lie in a "locked" state. Once a user touches a touch sensitive control area of the flexible linkage subassembly 42, the lens support subassembly 44, or the lens housing subassembly 49, the switching circuitry detects the electrical signal provided by the user's touch and activates the tension control mechanism 32, which mechanically unlocks the adjustable lens extension assembly 40, as described above. As the user grips the touch sensitive control area, the user is free to naturally move lens 18 to a desired position. Once the user has moved lens 18 to the desired location and has removed his or her grip from the touch sensitive control area, the switching circuitry detects the removal of the electrical signal provided by the user's touch and deactivates the tension control mechanism 32, thereby locking adjustable lens extension assembly 40 and the lens 18 in the desired location.

As will be appreciated by those familiar with touch sensitive switching circuitry, examples of which are discussed in U.S. Pat. No. 3,200,304 to Atkins; U.S. Pat. No. 3,254,313 to Atkins; and U.S. Pat. No. 3,715,540 to Larson, the relevant portions of which are incorporated herein by reference, the touch sensitive control area should be configured to provide an electrical signal in response to a user's touch. The touch sensitive control area and accompanying circuitry may employ technology that includes, but is not limited to, capacitance, resistance, frequency, and/or voltage detection to change the state of the switching circuitry.

Figure 9:
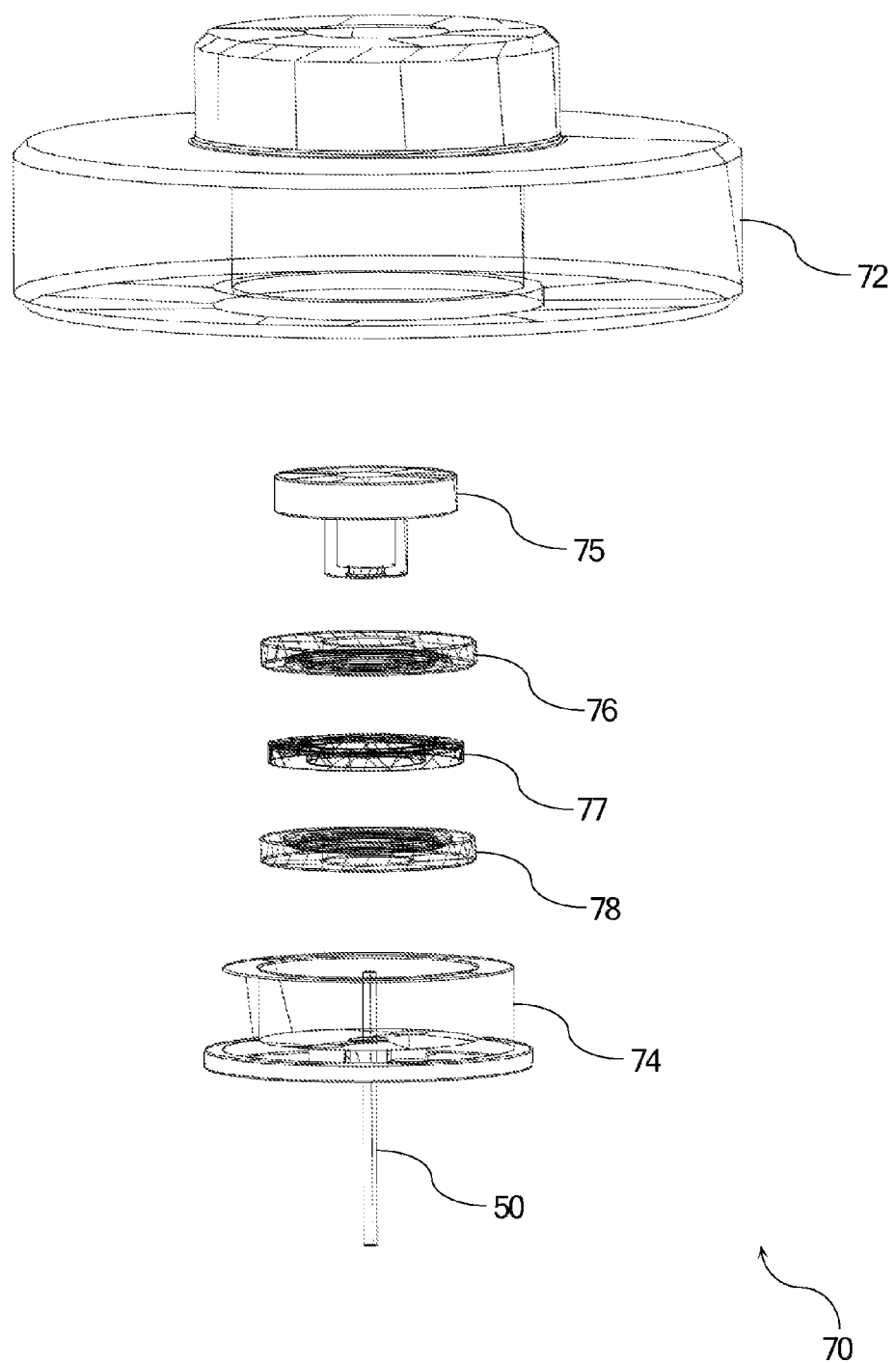
FIG. 9 is an exploded view of the thrust bearing subassembly illustrated in FIG. 8.

As is noted above, the tension control assembly 30 comprises a thrust bearing subassembly 70 that is secured to opposing ends of the tensile cord 50 and a solenoid plunger 34 of the tension control assembly 30. Referring to FIG. 9, the thrust bearing subassembly 70 comprises a thumb screw 72 and screw stop 74 that are configured for selective coupling and decoupling of the tensile cord 50 to the tension control assembly 30. The thrust bearing assembly further comprises a sleeve stop 75, a thrust plate 76, a bearing race 77, and a thrust plate 78. Generally, the thrust bearing subassembly 70 secures the end portion of the tensile cord 50 and permit translation of the tensile cord 50 from the relatively taut state, when a tension control mechanism 32 of the tension control assembly 30 is deactivated, to a relatively relaxed state, when the tension control mechanism 32 is activated.

It is noted that recitations herein of a component of the present invention being "configured" in a particular way, "configured" to embody a particular property or function in a particular manner, are structural recitations as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present invention or to emphasize alternative or additional features that may or may not be utilized in a particular embodiment of the present invention.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention may be identified herein as preferred or particularly advantageous, it is contemplated that the present invention is not necessarily limited to these preferred aspects of the invention.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A positioning device comprising a first lens positioning assembly and a second lens positioning assembly, wherein:
   the first lens positioning assembly comprises a lens support subassembly and a bi-directional positioning guide;
   the lens support subassembly comprises a translating rod;
   the bi-directional positioning guide comprises a coiled spring defining an inner periphery;
   the coiled spring is canted relative to a longitudinal axis of the rod;
   the inner periphery of the coiled spring engages in a spring loaded state an outer periphery of the rod such that the coiled spring provides a frictional force about the outer periphery of the rod;
   the frictional force provided by the coiled spring about the outer periphery of the rod is sufficient to hold the rod within the inner periphery, but permit infinitely variable bi-directional movement of the rod through the inner periphery under an applied force;
   the second lens positioning assembly comprises an electromagnetic linear actuator comprising a stationary component and a bi-directionally moveable component electromagnetically coupled to each other; and
   the electromagnetic linear actuator of the second lens positioning assembly is configured to adjust bi-directionally a position of the lens support subassembly of the first lens positioning assembly relative to a vertical position of a lens supported by the lens support subassembly.

2. The positioning device of claim 1, wherein the bi-directional movement of the translating rod through the inner periphery of the positioning guide and the bi-directional adjustment of the first lens positioning assembly by the electromagnetic linear actuator are along parallel axes.

3. The positioning device of claim 1, wherein the translating rod comprises a first end configured to engage the inner periphery of the coiled spring of the positioning guide and a second end configured to support a lens.

4. The positioning device of claim 1, wherein:
   the lens support subassembly further comprises a lens positioning hinge comprising an elastomeric cord configured to permit movement of the lens from a viewing position to a folded position away from the viewing position; and
   the elastomeric cord provides a degree of flexibility sufficient to permit movement of the lens between the viewing position and the folded position.

5. The positioning device of claim 1, wherein the moveable component of the electromagnetic linear actuator of the second lens assembly is mechanically coupled to the positioning guide of the first lens positioning assembly such that bi-directional movement of the moveable component correspondingly adjusts the position of the lens support subassembly.

6. The positioning device of claim 1, wherein the second lens positioning assembly comprises a fine adjustment assembly configured to control the bi-directional movement of the moveable component, the fine adjustment assembly comprising a fine adjustment up switch and a fine adjustment down switch, both electrically coupled to the electromagnetic linear actuator.

7. The positioning device of claim 1, wherein the electromagnetic linear actuator of the second lens positioning assembly comprises a voice coil actuator.

8. The positioning device of claim 1, wherein the electromagnetic linear actuator of the second lens positioning assembly comprises a piezo-electric actuator.

9. The positioning device of claim 1, wherein the second lens positioning assembly is not susceptible to screw-backlash.

10. The positioning device of claim 1, wherein the second lens positioning assembly does not include a motor, a lead screw, or other geared mechanism.

11. The positioning device of claim 1, wherein the second lens positioning assembly comprises an extension subassembly coupled to the bi-directional positioning guide of the first lens positioning assembly.

12. The positioning device of claim 1 further comprising a power and control assembly configured to control an operation of the electromagnetic linear actuator.

13. The positioning device of claim 12, wherein the power and control assembly comprises:
 an input device configured to transmit commands inputted by an operator of the positioning device,
 a processor configured to process the commands received from the input device into instructions for the operation of the electromagnetic linear actuator, and
 a power generator configured to generate power sufficient to operate the electromagnetic linear actuator.

14. The positioning device of claim 13, wherein the input device comprises a footswitch comprising one or more pedals.

15. A microscope comprising a non-contact ophthalmic surgical microscope assembly, a first lens positioning assembly, and a second lens positioning assembly, wherein:
 the first lens positioning assembly comprises a lens support subassembly and a bi-directional positioning guide;
 the lens support subassembly comprises a translating rod;
 the bi-directional positioning guide comprises a coiled spring defining an inner periphery;
 the coiled spring is canted relative to a longitudinal axis of the rod;
 the inner periphery of the coiled spring engages in a spring loaded state an outer periphery of the rod such that the coiled spring provides a frictional force about the outer periphery of the rod;
 the frictional force provided by the coiled spring about the outer periphery of the rod is sufficient to hold the rod within the inner periphery, but permit infinitely variable bi-directional movement of the rod through the inner periphery under an applied force;
 the second lens positioning assembly comprises an electromagnetic linear actuator comprising a stationary component and a bi-directionally moveable component electromagnetically coupled to each other; and
 the electromagnetic linear actuator of the second lens positioning assembly is configured to adjust bi-directionally a position of the lens support subassembly of the first lens positioning assembly relative to a vertical position of a lens supported by the lens support subassembly.

16. A microscope comprising a microscope assembly and a lens positioning assembly, wherein:
 the lens positioning assembly comprises a lens support subassembly and a bi-directional positioning guide;
 the lens support subassembly comprises a translating rod;
 the bi-directional positioning guide comprises a coiled spring wound about a circumscribed axis that extends around the translating rod to define an inner periphery;
 the circumscribed axis and the inner periphery of the coiled spring are concentric;
 the coiled spring is canted relative to a longitudinal axis of the rod;
 the inner periphery of the coiled spring engages in a spring loaded state an outer periphery of the rod such that the coiled spring provides a frictional force about the outer periphery of the rod; and
 the frictional force provided by the coiled spring about the outer periphery of the rod is sufficient to hold the rod within the inner periphery, but permit infinitely variable bi-directional movement of the rod through the inner periphery under an applied force.

17. The microscope of claim 16, wherein the microscope further comprises a second lens positioning assembly.

\* \* \* \* \*